US005639453A

United States Patent [19]
Clark et al.

[11] Patent Number: 5,639,453
[45] Date of Patent: Jun. 17, 1997

[54] THERAPEUTIC USES OF IL-3

[75] Inventors: Steven C. Clark, Winchester; Agnes B. Ciarletta, Haverhill, both of Mass.; Yu-Chung Yang, Indianapolis, Ind.

[73] Assignee: Genetics Institute, Inc., Cambridge, Mass.

[21] Appl. No.: 370,277

[22] Filed: Jan. 10, 1995

Related U.S. Application Data

[63] Continuation of Ser. No. 826,576, Jan. 27, 1992, abandoned, which is a continuation of Ser. No. 554,039, Jul. 17, 1990, abandoned, which is a division of Ser. No. 21,865, Mar. 4, 1987, Pat. No. 4,959,455, which is a continuation-in-part of Ser. No. 885,060, Jul. 14, 1986, abandoned, Ser. No. 893, 764, Aug. 6, 1986, abandoned, and Ser. No. 916,335, Oct. 7, 1986, Pat. No. 4,877,729.

[51] Int. Cl.$^6$ .................... A61K 38/20; C07K 14/54
[52] U.S. Cl. .................... 424/85.2; 514/2; 514/8; 514/12; 514/885
[58] Field of Search .................... 424/85.2; 514/2, 514/8, 12, 21, 885

[56] References Cited

U.S. PATENT DOCUMENTS

| 4,658,018 | 4/1987 | Urdal et al. | 530/351 |
| 4,695,542 | 9/1987 | Yokota et al. | 435/172.3 |
| 4,877,729 | 10/1989 | Clark | 435/68 |

FOREIGN PATENT DOCUMENTS

| 59-62336 | 3/1984 | Japan . |
| 59-62335 | 3/1984 | Japan . |
| 60-207594 | 10/1985 | Japan . |
| 60-207595 | 10/1985 | Japan . |
| WO85/02863 | 7/1985 | WIPO . |
| WO88/04691 | 6/1988 | WIPO . |
| WO88/05469 | 7/1988 | WIPO . |
| WO88/06161 | 8/1988 | WIPO . |

OTHER PUBLICATIONS

Gianella-Borradori, Stem Cells 12(Suppl 1):241–248 (1994).
D'Hondt et al., J. Clin. Oncol. 11(11):2063–2071 (1993).
Tepler et al., Br. J. Haematol. 87:678–686 (1994).
Boston Globe, / Oct. 1986, "Major find in blood science is reported" 230(99):1,11.
New York Times, 7 Oct. 1986, "Researchers Find Important Factor In Blood Growth" cxxxvi(46,920):p.C3.
Stadler et al, 1986, "Biological and Biochemical Characteristics of . . . (BaPA) . . . ," *Immunobiol.*, 172:225–230.
Suzuki et al, Nov. 1986, "Production of a Cytokine . . . ," *J. Exp. Med.*, 164:1682–1699.
Stadler et al, 1986, "Distinction of the Human Basophil Promoting Activity from Interleukin-3" Int. Archs Allergy Appl., *Immunology*, 77:151–154.
Stadler & Hirai, 1988, "Human growth Factors for Metachromatically Staining Cells," *Lymphokines*, vol. 15, pp. 341–354.

Hirai, de Weck & Stadler, 1988, "Characterization of a Human Basophil–like Cell Promoting Activity": *J. Immunol.*, 140:221–227.
Godard et al, 1988, "Biochemical Characterization and Purification of Hilda . . . ," *Blood*, 71(6):1618–1623.
Ihle, 1985, "Immunological Regulation of Hematopoietic Stem Cell Differentiation by Interleukin-3" in the Year in Immunology, 1984–1985, pp. 107–117.
Cohen et al, 1986, "Cloning and expression of the rat interleukin-3 gene", *Nucleic Acids Research*, 14(9):3641–3658.
Kindler et al, 1986, "Stimulation of hematopoiesis . . . ", *Proc. Natl. Acad. Sci.*, USA, 83:1001–1005.
Emerson et al, 1985, "Purification of Fetal Hematopoietic Progenitors . . . " J. Clin. Invest., 76:1286–1290.
Yang et al, 10 Oct. 1986, "Human IL-3 . . . ", *Cell*, 47:3–10.
Griffin et al, 1984, "Induction of Proliferation . . . Granulocyte Colony–Stimulating Factors", *Blood*, 63(4):904–911.
Rennick et al, 1985, "A Cloned MCGF cDNA . . . ", *J. Immunol.*, 134(2):910–912.
Hapel et al, 1985, "Biologic Properties of Molecularly Cloned and Expressed Murine Interleukin-3", *Blood*, 65(6):1453–1459.
Miyatake et al. 1985, "Structure of the chromosomal gene for murine interleukin 3", Proc. Natl. Acad. Sci. USA, 82:316–320.
Dexter, 1984, "The message is the medium", *Nature*, 309:746–747.
Clark–Lewis, 1986, "Automated Chemical Synthesis of . . . Interleukin 3", *Science*, 231:134–139 [Chemical synthesis of murine IL-3].
Metcalf et al, 1986, "Effects of . . . Murine . . . IL-3 . . . ", *Blood*, 68(1):46–57.
Birchenall–Sparks et al, 25 Jul. 1986, "Regulation of . . . by Interleukin–" *Science*, 233:455–458.
Palacios & Garland, 1984, ". . . interleukin 3 . . . ", *Proc. Natl. Acad. Sci. USA*, 81:1208–1211.
Scott et al, 1981, "Molecular cloning . . . ", *Proc. Natl. Acad. Sci. USA*, 78(7):4213–4217.
Quesenberry et al, 1985, "The Effect of Interleukin 3 . . . ", *Blood*, 65(1):214–217.
Metcalf et al, 1985, "Synthesis by Mouse . . . ", *Leukemia Research*, 9(1):35–50.
Chen et al, Jul. 15, 1986, "Interleukin 3 . . . ", *J. Immunol.*, 137(2):563–570.
Jubinsky et al, 1985, "Purification of hematopoietin 1 . . . ", *Proc. Natl. Acad. Sci.*, USA, 82:2764–2768.
Goossens et al, Methods In Enzymology vol. 76 pp. 805–817 (1981).
Conlon et al, The J of Immunology vol. 135 pp. 328–332 Jul. 1985.

(List continued on next page.)

*Primary Examiner*—John Ulm
*Assistant Examiner*—Prema Mertz
*Attorney, Agent, or Firm*—Steven R. Lazar; Thomas J. DesRosier

[57] ABSTRACT

A method of treating leukopenia, by administering an IL-3 polypeptide, is disclosed.

4 Claims, No Drawings

OTHER PUBLICATIONS

Ihle et al, The J of Immunology vol. 131 pp. 282–287 (1983).
Stadler et al, Chemical Abstracts vol. 106 16853y (1987).
Suzuki et al, Chemical Abstracts vol. 105 224285w (1986).
Stadler et al, Chemical Abstracts vol. 103 525575f (1985).
D.M. Rennick, et al., *J. Immunol.*, 134(2):910–914 (Feb. 1985).
H.D. Campbell, et al., *Eur. J. Biochem.*, 150:297–304 (1985).
M.C. Fung, et al., *Nature*, 307:233–237 (Jan. 1984).
T. Yokota, et al., *Proc. Natl Acad. Sci. USA*, 81:1070–1074 (Feb. 1984).
Goossens, et al., *Methods in Immunology*, 76:805–817 (1981).
A.A. Ythier, et al., *Proc. Natl. Acad. Sci., USA*, 82:7020–7024 (Oct. 1985).
R. Palacio, *J. Immunol.*, 132(4):1833–1836 (Apr. 1984).
Palacios and Garland, *Proc. Natl. Acad. Sci., USA*, 81:1208–1211 (1984).
Scott, et al., *Proc. Natl. Acad. Sci. USA*, 78(7):4213–4217 (1984).
A.F. Lopez, et al., *Proc. Natl. Acad Sci USA*, 84:2761–2765 (May 1987).
A.G. Leary, et al., *Blood*, 70:1343–1348 (1987).
Gallicchio et al *Expl Cell Biol* 55, 1987, pp. 83–92.
Broxmeyer et al PNAS 84, 1987 pp. 3871–3875.
Clark et al *Science* 236, 1987, p. 1229.
Burgess et al. Blood 1980, vol. 56, pp. 947–958.
Bowlin et al, *J Immunol* 133(4) 1984, pp. 2001–2006.
Garnick, et al., *Hematology/Oncology Clinics of North America* 3(3):495–509 (Sep. 1989).
Gillio, et al., *Blood* 72, suppl.:117a, Abstract 380 (1988).
Robinson, et al., *Am. J. Med. Sci.* 300(5):311–321 (Nov. 1990).
Ganser, et al, *Blood* 74(7), suppl.:50a, Abstract 177 (Nov. 1989).
Whetton, *TiPS* 11:285–289 (Jul. 1990).
Broxmeyer, et al., *Immunol. Res.* 8:185–201 (1989).

THERAPEUTIC USES OF IL-3

This is a continuation of application Ser. No. 07/826,576, filed Jan. 27, 1992 and now abandoned, which in turn is a continuation of application Ser. No. 07/554,039, filed Jul. 17, 1990 and now abandoned, which in turn is a division of application Ser. No. 07/021,865, filed Mar. 4, 1987 and now U.S. Pat. No. 4,959,455, which in turn is a continuation-in-part of applications Ser. Nos. 06/885,060, filed Jul. 14, 1986 and now abandoned, 06/893,764, filed Aug. 6, 1986 and now abandoned and 06/916,335, filed Oct. 7, 1986 and now U.S. Pat. No. 4,877,729.

BACKGROUND

Hematopoietins, i.e., hematopoietic growth factors, are proteins that promote the survival, growth and differentiation of hematopoietic cells. Colony stimulating factors (CSFs) are a subset of these hematopoietic growth factors that are characterized by the ability to support the growth, in vitro, of colonies of hematopoietic cells arising from progenitor cells of bone marrow, fetal liver, and other hematopoietic organs.

The biochemical and biological identification and characterization of certain hematopoietins has been hampered by the small quantities of the naturally occurring factors available from natural sources, e.g., blood and urine. With recombinant genetic engineering techniques, however, some of these hematopoietins have been molecularly cloned, heterologously expressed and purified to homogeneity. [See D. Metcalf, "The Molecular Biology and Functions of the Granulocyte-Macrophage Colony Stimulating Factors," Blood, 67(2):257–267 (1986).] Among these hematopoietins are human and murine GM-CSF, human G-CSF, human CSF-1 and murine IL-3. Both human GM-CSF [See, R. Donahue et al., Nature, 321:872–875 (1986)] and murine IL-3 [See J. Kindler et al, Proc. Natl. Acad. Sci. U.S.A., 83:1001–1005 (1986), and Metcalf et al., Blood, 68:46–57 (1986)] have a demonstrated effect on hematopoiesis in vivo. The murine protein IL-3 has heretofore been found to have no duplicate in the human system. [See, D. R. Cohen et al, Nucl. Acids Res., 14:3641 (1986).]

BRIEF SUMMARY OF THE INVENTION

As one aspect of the invention, a family of primate IL-3-like growth factors is provided. These growth factors are substantially free of association with other primate proteins and are characterized by amino acid sequences substantially homologous to the sequence shown in Tables I and II below. The amino acid sequences of the growth factors of the present invention are encoded by the DNA sequences of Tables I and II. Additionally, members of this family of growth factors are coded for by DNA sequences which hybridize under stringent hybridization conditions to the DNA sequences of Tables I and II.

DNA sequences which hybridize to the sequences of Tables I or II under relaxed hybridization conditions and which code on expression for growth factors having primate IL-3-like biological properties also encode members of this family of novel growth factors. For example, a DNA sequence which shares regions of significant homology, e.g., sites of glycosylation or disulfide linkages, with the sequences of Tables I and/or II and encodes a primate protein having one or more IL-3-like biological properties clearly encodes a member of this novel family of growth factors, even if such a DNA sequence would not stringently hybridize to the sequence of Table I or II.

Similarly, DNA sequences which code for primate polypeptides coded for by the sequence of Table I or II or sequences which hybridize thereto, but which differ in codon sequence due to the degeneracies of the genetic code or differ in nucleotide sequence due to cross-species variation or induced modifications also encode the novel growth factors of this family described herein.

In addition to the DNA sequence homology to the sequences of Tables I and II, the members of this novel family of growth factors are also characterized by having at least one biological property of an IL-3-like growth factor. Preferably more than one IL-3-like biological property is demonstrated by any one member of the family of growth factors of the present invention. "IL-3-like biological property" is defined herein to include one or more of the following biological characteristics and in vivo and in vitro activities.

One such property is the support of the growth and differentiation of progenitor cells committed to erythroid, lymphoid, and myeloid lineages. For example, in a standard human bone marrow assay, an IL-3-like biological property is the stimulation of granulocytic type colonies and erythroid bursts. Another such property is the interaction with early multipotential stem cells.

An IL-3-like biological property is the sustaining of the growth of pluripotent precursor cells. Another property is the ability to stimulate chronic myelogenous leukemia (CML) cell proliferation. An IL-3-like biological property also is the stimulation of proliferation of mast cells. IL-3-like growth factors may also support the growth of various factor-dependent cell lines and/or induce the expression of 20-alpha-steroid dehydrogenase (20-alpha-SPH) and Thy-1 antigen. Further IL-3-like biological properties are the stimulation of colony formation on KG-1 cells and/or the stimulation of increased histamine synthesis in spleen and bone marrow cultures. Yet another IL-3 biological property is an apparent molecular weight of between about 14 to about 35 kd by reducing sodium dodecyl sulfate polyacrylamide gel electrophoresis. Other biological properties of IL-3 have been disclosed in the art.

As a further aspect of the present invention there are provided novel DNA sequences, free of association with DNA sequences encoding other primate proteins, and coding on expression for primate IL-3-like polypeptides or growth factors. These DNA sequences include those depicted in Table I and Table II in a 5' to 3' direction and those sequences described above. Variations in the DNA sequences of Tables I and II which are caused by point mutations or by induced modifications to enhance the activity, half-life or production of the polypeptides are also encompassed in the invention. Similarly, synthetic polypeptides which wholly or partially duplicate continuous sequences of the amino acid residues of Tables I and II are also part of this invention. These sequences, by virtue of sharing primary, secondary, or tertiary structural and conformational characteristics with naturally-occurring primate IL-3-like polypeptides of the invention may possess biological activity and/or immunological properties in common with the naturally-occurring product. Thus, they may be employed as biologically active or immunological substitutes for naturally-occurring primate IL-3-like polypeptides in therapeutic and immunological processes.

As another aspect of the present invention, there is provided a novel method for producing the novel family of primate IL-3-like growth factors. The method of the present invention involves culturing a suitable cell or cell line, which has been transformed with a vector containing a DNA sequence coding on expression for a novel primate IL-3-like polypeptide. Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Another suitable mammalian cell line, which is described in the accompanying examples, is the monkey COS-1 cell line. A similarly useful mammalian cell line is the CV-1 cell line. Also suitable for use in the present invention are bacterial cells. For example, the various strains of *E. coli* are well-known as host cells in the field of biotechnology. Various strains of *B. subtills* may also be employed in this method. Many strains of yeast cells known to those skilled in the art are also available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel primate polypeptides. These vectors contain the novel DNA sequences described above which code for the novel polypeptides of the invention. Alternatively, vectors incorporating modified sequences as described above are also embodiments of the present invention and useful in the production of these IL-3-like polypeptides. The vector employed in the method also contains selected regulatory sequences in operative association with the DNA coding sequences of the invention and capable of directing the replication and expression thereof in selected host cells.

The members of the novel family of primate IL-3-like growth factors may be used in the treatment of diseases, characterized by a decreased level of either myeloid, erythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs. Therapeutic treatment of leukopenia with these IL-3-like polypeptide compositions may avoid undesirable side effects caused by treatment with presently available drugs.

Various immunodeficiencies e.g., in T and/or B lymphocytes, or immune disorders, e.g., rheumatoid arthritis, may also be beneficially effected by treatment with the polypeptides of the present invention. Immunodeficiencies may be the result of viral infections e.g. HTLVI, HTLVII, HTLVIII, severe exposure to radiation, cancer therapy or the result of other medical treatment. The polypeptides of the present invention may also be employed, alone or in combination with other hematopoietins, in the treatment of other blood cell deficiencies, including thrombocytopenia (platelet deficiency), or anemia (red cell deficiency). Other uses for these novel polypeptides are in the treatment of patients recovering from bone marrow transplants, and in the development of monoclonal and polyclonal antibodies generated by standard methods for diagnostic or therapeutic use.

Therefore, as yet another aspect of the invention are methods and therapeutic compositions for treating the conditions referred to above. Such compositions comprise a therapeutically effective amount of one or more of the members of the family of primate IL-3-like polypeptides of the present invention in admixture with a pharmaceutically acceptable carrier. This composition can be systematically administered either parenterally, intravenously or subcutaneously. When systematically administered, the therapeutic composition for use in this invention is, of course, in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, the daily regimen should be in the range of 200–1000 micrograms of polypeptide or 50 to 5000 units (ie, a unit being the concentration of polypeptide which leads to half maximal stimulation in a standard human bone marrow assay) of polypeptide per kilogram of body weight. The therapeutic method and compositions may also include co-administration with other human factors. A non-exclusive list of other appropriate hematopoietins, CSFs and interleukins for simultaneous or serial co-administration with the polypeptides of the present invention includes GM-CSF, CSF-1, G-CSF, Meg-CSF, erythropoietin (EPO), IL-1, IL-4, IL-2, B-cell growth factor, B-cell differentiation factor and eosinophil differentiation factor. The dosage recited above would be adjusted to compensate for such additional components in the therapeutic composition. Progress of the treated patient can be monitored by periodic assessment of the hematological profile, e.g. white cell count and the like.

DETAILED DESCRIPTION OF THE INVENTION

The present invention provides a family of primate IL-3-like growth factors substantially free from other primate proteins and characterized by amino acid sequences substantially homologous to the amino acid sequences illustrated in Tables I and II below. These sequences may be encoded by the DNA sequences depicted in the Tables or sequences capable of hybridizing thereto and coding for polypeptides with IL-3-like biological properties or variously modified sequences as described above. These polypeptides are also characterized by IL-3-like biological properties.

The specific sequences illustrated in Tables I and II are two exemplary members of the growth factor family of the present invention. The 865 bp DNA sequence of Table I was isolated from a cDNA expression library of the gibbon ape leukemia virus infected gibbon T-cell line UCD-144-MLA [T. G. Kuwakami et al, *Nature*, 235:170 (1972)]. This sequence contains a single long open reading frame of 456 nucleotides which encodes an approximately 152 amino acid protein, called CSF-80, and includes a conventional leader secretory sequence indicated by the highly hydrophobic sequence (leu leu leu leu gln leu leu). The mature protein begins at amino acid number 20, alanine, in Table I. The coding region contains three cysteines, two in the mature protein, thereby suggesting one disulfide bond. There are two potential asparagine-linked glycosylation sites illustrated by the characteristic sequences, Asn-X-Ser or Asn-X-

Thr. Both the size and glycosylation pattern revealed by the coding sequence are typical of lymphokine-like proteins. The remaining non-coding portions of the 865 bp region may have a regulatory role in transcription in the natural host. The 3' end of the sequence also contains an AT-rich segment including several repeats of the sequence ATTTA, which is believed to be related to the RNA message stability [See, G. Shaw and R. Kamen, *Cell*, 46 (5): 659–677 (1986)].

TABLE I a

```
           10          20          30
CTCGAGCTAC GTCAACGAAA AATAAAATCC AAAC ATG AGC TGC
                                      MET Ser Cys 49                      64                  79
CTG CCC GTC CTG CTC CTG CTC CAA CTC CTG GTC AGC CCC
Leu Pro Val Leu Leu Leu Leu Gln Leu Leu Val Ser Pro 94                  109
GGA CTC CAA GCT CCC ATG ACC CAG ACA ACG TCC TTG AAG
Gly Leu Gln Ala Pro MET The Gln Thr Thr Ser Leu Lys

124                 ——139——              154
ACA AGC TGG GTT AAC TGT TCT AAC ATG ATC GAT GAA ATT
Thr Ser Trp Val Asn Cys Ser Asn Met Ile Asp Glu Ile 169                 184              199
ATA ACA CAC TTA AAG CAG CCA CCT TTG CCC TTG CTG GAC
Ile Thr His Leu Lys Gln Pro Pro Leu Pro Leu Leu Asp 214                 229
TTC AAC AAC CTC AAT GGG GAA GAC CAA GAC ATT CTG ATG
Phe Asn Asn Leu Asn Gly Glu Asp Gln Asp Ile Leu MET 244                 259                 274
GAA AAT AAC CTT CGA AGG CCA AAC CTG GAG GCA TTC AAC
Glu Asn Asn Leu Arg Arg Pro Asn Leu Glu Ala Phe Asn

289                  ——304——
AAG GCT GTC AAG AGT TTA CAG AAT GCA TCA GCA ATC GAG
Lys Ala Val Lys Ser Leu Gln Asn Ala Ser Ala Ile Glu 319                 334                 349
AGC ATT CTT AAG AAT CTC CCC CCA TGC CTG CCC ATG GCC
Ser Ile Leu Lys Asn Leu Pro Pro Cys Leu Pro MET Ala 364                 379              394
ACA GCC GCA CCC ACG CGA CAT CCA ATC CGT ATC AAG GAC
Thr Ala Ala Pro Thr Arg His Pro Ile Arg Ile Lys Asp 409                 424
GGT GAC TGG AAT GAA TTC CGG AGG AAA CTG AAG TTC TAT
Gly Asp Trp Asn Glu Phe Arg Arg Lys Leu Lys Phe Tyr
``` b

```
    439                 454                 469
CTG AAA ACC CTT GAG AAT GAG CAA GCT CAA CAG ATG ACT
Leu Lys Thr Leu Glu Asn Glu Gln Ala Gln Gln MET Thr 484                 500         510
TTG AGC CTT GAG ATC TCT TGAGTCCAAC GTCCAGCTCT
Leu Ser Leu Glu Ile Ser 520        530        540        550
CTCTCTGGGC CGTCTCACCG CAGAGCCTCA GGACATCAAA 560        570        580        590
AACAGCAGAA CTTCTGAAAC CTCTGGGTCG TCTCTCACAC 600        610        620        630
AGTCCAGGAC CAGAAGCATT TCACCTTTTC CTGCGGCATC 640        650        660        670
AGATGAATTG TTAATTATCT AATTTCTGAA ATGTGCAGCT 680        690        700        710
CCCATTTGGC CTTGTGTGGT TGTGTTCTCA TTTTTATCCC 720        730        740        750
ATTGAGACTA TTTATGTATG TCTGTATTTA TTTATTTATT
```

TABLE I-continued

```
         760        770        780        790
TATTTATTGC CTTCTGGAGC GTGAAGTGTA TTTATTTCAG 800        810        820        830
CAGAGGAGCC ATGTCATGCT GCTTCTGCAA AAAACTCAAG 840        850        860
AGTGGGGTGG GGAGCATGTT CATTTGTACC TCGAG
```

The 674 bp DNA sequence of Table II was obtained from a human genomic library [J. J. Toole et al, *Nature*, 312:342–346 (1984)] by employing the sequence of Table I as a probe. The DNA sequence of Table II was initially constructed by splicing together the exons of the human genomic sequence, which were identified by comparison with the DNA sequence of the gibbon IL-3-like polypeptide of Table I. This human sequence confirmed by mRNA analysis of the human cDNA clone also codes for a polypeptide of approximately 152 amino acids, which is a member of this family of primate proteins. This human polypeptide includes a conventional leader secretory sequence indicated by the highly hydrophobic sequence (leu leu leu gln leu leu). The mature polypeptide begins at amino acid number 20, alanine, in Table II. The coding region contains two cysteines in the mature protein, suggesting one disulfide bond. There are two potential asparagine-linked glycosylation sites illustrated by the characteristic sequence, Asn-X-Ser. The remaining noncoding portions of the 674 bp sequence may have a regulatory role in transcription in the natural host.

TABLE II

```
                        a
                        ─
A         9           T           24                          39
GATCCAAAC ATG AGC CGC CTG CCC GTC CTG CTC CTG CTC
          MET Ser Arg Leu Pro Val Leu Leu Leu Leu
                  Cys                              10

A                         69
CAA CTC CTG GTC CGC CCC GGA CTC CAA GCT CCC ATG ACC
Gln Leu Leu Val Arg Pro Gly Leu Gln Ala Pro MET Thr
                Ser                    20

84                   99            ─── T ───
CAG ACA ACG TCC TTG AAG ACA AGC TGG GTT AAC TGC TCT
Gln Thr Thr Ser Leu Lys Thr Ser Trp Val Asn Cys Ser
                             30                    ─────────

129                144
AAC ATG ATC GAT GAA ATT ATA ACA CAC TTA AAG CAG CCA
Asn MET Ile Asp Glu Ile Ile Thr His Leu Lys Gln Pro
             40

159          C          174                189
CCT TTG CCT TTG CTG GAC TTC AAC AAC CTC AAT GGG GAA
Pro Leu Pro Leu Leu Asp Phe Asn Asn Leu Asn Gly Glu
50                                                60

204                   219                234
GAC CAA GAC ATT CTG ATG GAA AAT AAC CTT CGA AGG CCA
Asp Gln Asp Ile Leu MET Glu Asn Asn Leu Arg Arg Pro
                                70

.    249      A        264
AAC CTG GAG GCA TTC AAC AGG GCT GTC AAG AGT TTA CAG
Asn Leu Glu Ala Phe Asn Arg Ala Val Lys Ser Leu Gln
                     80      Lys

─T    279 ───         C        294         G      309   CC
AAC GCA TCA GCA ATT GAG AGC ATT CTT AAA AAT CTC CTG
Asn Ala Ser Ala Ile Glu Ser Ile Leu Lys Asn Leu Leu
───── 90 ─────                                   100 Pro

C       324 A       A        339
CCA TGT CTG CCC CTG GCC ACG GCC GCA CCC ACG CGA CAT
Pro Cys Leu Pro Leu Ala Thr Ala Ala Pro Thr Arg His
                MET                 110
```

TABLE II-continued

```
354        G           369                      384
CCA ATC CAT ATC AAG GAC GGT GAC TGG AAT GAA TTC CGG
Pro Ile His Ile Lys Asp Gly Asp Trp Asn Glu Phe Arg
        Arg         120 b

399  A                 414                     A
AGG AAA CTG ACG TTC TAT CTG AAA ACC CTT GAG AAT GCG
Arg Lys Leu Thr Phe Tyr Leu Lys Thr Leu Glu Asn Ala
         130 Lys                                 Glu

A           T       450       T   A       C
CAG GCT CAA CAG ACG ACT TTG AGC CTC GCG ATC TTT
Gln Ala Gln Gln Thr Thr Leu Ser Leu Ala Ile Phe
                MET     147         Glu     Ser
                                        152

G       474           T C         494  G        G
T-AGTCCAAC GTCCAGCTCG TTCTCTGGGC CTTCTCACCA

A    A        524                       544
CAGCGCCTCG GGACATCAAA AACAGCAGAA CTTCTGAAAC

G          564  G                  584
CTCTGGGTCA TCTCTCACAC ATTCCAGGAC CAGAAGCATT 604                      624
TCACCTTTTC CTGCGGCATC AGATGAATTG TTAATTATCT

644                       T
AATTTCTGAA ATGTGCAGCT CCCATTTGGC CTTGTCGGT

674
TGTGTTCTCA
```

The nucleotide sequences of the exons of the human genomic gene [Table II] were more than 96% homologous with the DNA sequence of the gibbon gene [Table I]. Changes in the nucleotide sequences in 11 codons result in amino acid differences in the gibbon and human proteins. The nucleotides appearing above the sequence of Table II indicate the sites where the gibbon sequence differs from the related human sequence. Similarly, the amino acids appearing below the human amino acid sequence indicate where the gibbon sequence differs. The arrows indicate the sites of exon and intron junctions in the human genomic sequence.

A computer search by National Biomedical Services of Washington, D.C. revealed that the gibbon and human IL-3-like sequences have approximately 29% homology at the amino acid level and 45% homology at the nucleotide level to the murine IL-3 DNA sequence, as published by M. C. Fung et al., Nature, 307:233–237 (1984). Exon structures of the human IL-3-like gene compared similarly with the coding regions of the murine IL-3.

The novel 865 bp cDNA sequence illustrated in Table I below, included in a plasmid in E. coli HB101, was deposited Jul. 11, 1986 in the Americantype Culture Collection, 12301 Parklawn Dr., Rockville, Md. and given accession number ATCC. 67154. The novel genomic sequence, for which the cDNA sequence is illustrated in Table II below, included in bacteriophage lambda, was similarly deposited Aug. 7, 1986 and given accession number ATCC 40246. The human IL-3 DNA included in plasmid pSHIL-3-1 in E. coli HB101 was deposited Feb. 24, 1987 in the ATCC and given accession number ATCC 67326. The exemplary human and gibbon IL-3-like polypeptides have been further characterized by SDS polyacrylamide gel analysis of the $^{35}$S-labeled proteins from transfected COS cells, as described below in the examples. Both polypeptides are heterogenous in size with molecular species having a range of apparent molecular weight of between about 14 kd–35 kd, and more specifically, 18 kd–30 kd. This range of molecular weights for these exemplary IL-3-like factors is believed to result from variations in glycosylation of the purified COS cell produced molecules. The purified proteins, at 10 to 100 picomolar concentrations, cause the formation of small granulocytic-type colonies in in vitro human bone marrow assays. Additionally, in the presence of erythropoietin in these human bone marrow assays both polypeptides support the growth of erythroid and myeloid progenitor cells at comparable levels of activity. Thus these IL-3-like factors are multi-CSFs. These IL-3-like factors also cause the proliferation of leukemic blast cells from patients with CML. These polypeptides may also be capable of stimulating accessory and mature cells, e.g. monocytes, to produce other hematopoietic-like factors, which in turn stimulate the formation of colonies of other hematopoietic cells, as well as other hematopoietic-type activities.

The family of IL-3-like growth factors provided herein also includes factors encoded by the sequences similar to those of Tables I and II, but into which nucleotide modifications are provided. For example, one such modified human sequence is a human cDNA sequence illustrated in Table I with the modification,of a proline encoded by the triplet CCC at amino acid #27 instead of the serine encoded by the triplet TCC which appears in the Table at that position. This exemplary modified cDNA sequence, which produces an active human IL-3-like factor, included in E. coli HB101 as pHucIL3-2, was deposited Jun. 30, 1989 in the A.T.C.C. under accession number ATCC 68042.

Other modifications in the DNA sequences can be made by one skilled in the art using known techniques. Specific modifications of interest in these IL-3-like related sequences include the replacement of one or both of the two cysteine residues in each coding sequence with other amino acids.

Preferably both cysteines are replaced with another amino acid, e.g. serine, to eliminate the disulfide bridge. Mutagenic techniques for such replacement are well known to one skilled in the art. [See, e.g., U.S. Pat. No. 4,518,584.]

Other specific mutations of the sequences of the IL-3-like factors described herein involve modifications of one or both of the glycosylation sites. The absence of glycosylation or only partial glycosylation results from amino acid substitution or deletion at one or both of the asparagine-linked glycosylation recognition sites present in the sequences of the IL-3-like factors shown in Tables I and II. The asparagine-linked glycosylation recognition sites. comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

For example, $Asn_{34}$ of the sequence of Table I can be replaced with glutamine in one such modified IL-3-like factor. The resulting factor ($Gln_{34}$) should contain only one asparagine-linked carbohydrate moiety (at $Asn_{89}$), rather than two such moieties. Those skilled in the art will appreciate that analogous glycoproteins having the same $Asn_{89}$ monoglycosylation may be prepared by substituting another amino acid at position 34, and/or by substituting another amino acid at the other positions within the glycosylation recognitions site, e.g., inserting valine at $Ser_{36}$. Similarly, the Asn at position 89 and/or Ser at position 91 may be altered by a mutagenic technique to other amino acids to deglycosylate the factor at that site. Alternatively, both sites may be altered as above. Such modifications to the glycosylation sites may also be made to create modifications of the sequence of Table II. [See, e.g. A. Miyajima et al., *EMBO J.*, 5(6):1993–1197 (1986) and Example IV below.]

The following examples illustratively describe members of the novel family of primate IL-3-like polypeptides and the methods of the present invention.

EXAMPLE I

Isolation of Gibbon IL-3-like Gene

A gibbon T-cell line infected with gibbon-ape leukemia virus, UCD-144-MLA, and available from the National Institute of Health Laboratories was induced with phytohemagglutinin and phorbol myristate acetate (PHA/PMA). Total RNA was prepared from these cells by the procedures of J. M. Chirgwin et al., *Biochem*, 18:5294 (1979). Poly $A^+$ mRNA was selected and fractionated on a 10% to 30% sucrose gradient. To identify the mRNA encoding this novel hematopoietic factor, sixteen aliquots of sucrose gradient-fractionated mRNA from the UCD-144-MLA cell line were micro-injected into *Xenopus laevis* oocytes and the resulting conditioned medium tested for the ability to stimulate the proliferation of leukemic blast cells in the presence of antibody to human GM-CSF as illustrated in the CML assay of Example V. mRNA from the sucrose gradient fractions identified as containing the message encoding IL-3-like growth factor activity was converted to double stranded cDNA by the procedure of U. Gubler and B. J. Hoffman, *Gene*, 25:263 (1983).

A COS cell expression vector, pXM, containing the SV40 enhancer, major adenovirus late promoter, DHFR coding sequence. SV40 late message poly A addition site and Val gene was linearized with the endonuclease enzyme XhoI, treated with DNA polymerase I large fragment in the presence of dTTP and ligated to equimolar amounts of cDNA, at a final DNA concentration of 100 ug/ml. The ligation products resulting from the XhoI digestion of pXM and the insertion of the XhoI adapted cDNA sequence were transformed into *E. coli* strain HB101 and plated on L+Amp plates to generate a library of approximately $30 \times 10^3$ colonies. [Other functionally similar expression vectors known in the art can also be used in this procedure as alternatives to pXM.]

The cDNA library in pXM was replica plated onto nitrocellulose filters. Colonies from each filter were scraped into L. broth, and plasmid DNA was isolated. Each DNA sample was prepared from a pool of 200–300 bacterial colonies. The DNA was purified by the method of J. A. Meyers et al., *J. Bacteriol*, 27:1529 (1976). Monkey COS cells (ATCC CRL 1650) were transfected with approximately 5 ug plasmid DNA per $10^6$ COS cells by DEAE mediated DNA transfection and treated with chloroquine according to the procedures described in G. G. Wong et al., *Science:* 228:810–815 (1985) and R. J. Kaufman et al. *Mol. Cell Biol.*, 2:1304 (1982).

72 hours following transfection, medium is harvested and assayed in the human CML assay, as described in Example V below. One pool produced conditioned medium with colony stimulating activity and CML proliferation activity completely resistant to neutralizing antiserumto GMCSF, and was selected for further analysis. Plasmid DNA from individual colonies picked from the original active pool was prepared and transfected to produce conditioned medium. This conditioned mediumwas assayed for CSF and CML proliferation activity. A single clone responsible for such activity was isolated. The cDNA insert of this clone was subcloned into M13 and was sequenced by the Sanger dideoxychain termination method. [See Table I]

EXAMPLE II

Isolation of a Human IL-3-like Gene

Using the sequence of Table I as a probe, $1 \times 10^6$ Clones from a human genomic library (Sau 3AI partial digest of human DNA cloned into the Bam HI site of the lambda vector J1) [J. J. Toole et al, supra] were screened. Three plaques were identified which contained sequences which hybridized strongly with the cDNA probe. The DNAs from two of these phages were digested to completion with the endonuclease enzyme Sau 3AI and subcloned into the Bam HI site of the bacteriophage lambda M13 cloning vector mp9. Subclones containing exon sequences were identified by hybridization with the gibbon cDNA. One subclone, lambda CSF-16, containing the human genomic DNA sequence as an approximately 10 kb Bgl II insert, was deposited with the ATCC as described above. The complete sequences of all of the exons of the human gene were determined using dideoxy chain termination DNA sequencing with a battery of oligonucleotide primers whose sequences were based upon the sequence of the gibbon gene described in Example I. Because the nucleotide sequences of the exons of the human gene were more than 96% homologous with the sequence of the gibbon cDNA, the nucleotide sequence of the corresponding human cDNA was reconstructed. Changes in the nucleotide sequences in 11 codons result in amino acid differences in the polypeptides from the two species. [See Table II].

The human genomic sequence can be excised from lambda CSF-16 and inserted into an expression vector, numerous types of which are known in the art for mammalian, insect, yeast, fungal, and bacterial expression. For example, the human genomic sequence was excised from the deposited bacteriophage by digestion with the endonucleases SmaI and XhoI which cleave the human gene region at nucleotides 629 and 3183 respectively. The resulting 2.5 kb contains the entire human IL-3 gene coding sequences and includes the "TATAA-related" sequence in the promoter region but lacks the "CAT-related" sequences and the polyadenylation signal at the 3' end of the gene. The SmaI end of this fragment was converted to XhoI with a commercially available linker sequence. This fragment was sub-cloned by standard molecular biology techniques [see, e.g., Y-C. Yang et al, Cell, 47:3–10 (1986)] into a XhoI-digested plasmid expression vector pXM, yielding plasmid pY3. pY3 was then amplified in bacteria and transfected into monkey COS-1 cells, where the human gene is transcribed and the RNA spliced. Media from the transfected cells is positive in assays for IL-3-like biological activity in the human bone marrow assay and the CML assay as described below. Northern blot analysis with a gibbon cDNA probe indicates the presence of a single 1 kbmRNA which is obtained from these cells and is the same size as RNA obtained from peripheral blood lymphocytes, as described below. cDNA is synthesized from the mRNA by standard procedures and a clone identified which has CML activity. cDNA for a novel IL-3-like growth factor was isolated therefrom.

EXAMPLE III

A Human IL-3-Like Growth Factor

The cDNA sequence of Table II encoding a human IL-3-like polypeptide may also be obtained in ways other than that described in Example II. For example, the sequence of Table II may be chemically synthesized according to procedures well known to those skilled in the art. One such chemical synthetic method involves reconstructing the gibbon IL-3 gene to provide the human IL-3 coding sequence. The first amino. acid difference between the mature forms of the gibbon and human IL-3 protein occurs at amino acid 82. The coding sequence from amino acid 82 in the gibbon IL-3 gene to the 3'-end of the gene can be replaced by chemically synthesized DNA sequences encoding for human IL-3, thereby yielding a functional gene capable of producing human IL-3 in a suitable expression system.

Two unique restriction sites in the gibbon sequence can be used for cloning synthetic sections of DNA: an Asu II site at amino acid 73 and EcoRI at amino acid 125. A DNA "cassette" for insertion into the gibbon gene was synthesized from the Asu II site to the EcoRI by enzymatically providing a DNA duplex of approximately 160 bp from two oligonucleotides which are complementary to each other over 21 base pairs. The complete duplex was formed by extending the complementary region to the ends of the oligonucleotides using deoxynucleoside triphosphates and DNA polymerase I, Klenow fragment. The complete duplex was digested with Asu II and/or EcoRI to yield cohesive ends for subsequent cloning.

A second synthetic DNA "cassette" consists of two oligonucleotides, complementary to each other throughout their length, from the EcoRI site at amino acid 125 to, and including, the termination codon following amino acid 152 at the end of the gene. These oligos were designed with an EcoRI cohesive end and suitable restriction sites or cohesive ends at or just after the termination codon for cloning into different expression vectors.

Two sets of these cassettes were synthesized, one set for mammalian expression, the other for bacterial expression responsive to differences in codon usage between prokaryotes and eukaryotes, the low incidence of CpG doublets in eukaryotic genes and retention of, or the need for, different restriction sites for cloning. Such codon preferences are known to those skilled in the art. See, e.g., T. Maruyama et al., Nucl. Acids Res., 14:r151 (1986). Exemplary codon changes and cohesive ends synthesized for these cassettes appear in Table III below. The cassettes are then cloned into the vector, pCSF-MLA, to transform it into a vector bearing the gene encoding the human IL-3-like factor. This resulting vector is then used to express the human factor.

TABLE III

I. CODON CHANGES

| Amino acid # | Bacterial expression | Mammalian expression |
|---|---|---|
| 73 | CGT | |
| 74 | CGT | |
| 75 | CCG | |
| 82 | CGT | |
| 86 | AGC | |
| 87 | CTG | CTG |
| 88 | CAA | CAA |
| 89 | | AAT |
| 91 | AGC | |
| 97 | CTG | CTG |
| 100 | CTG | CTG |
| 102 | CCG | |
| 105 | CCG | |
| 108 | ACC | ACA |
| 109 | | GCT |
| 111 | CCG | |
| 112 | ACC | ACC |
| 113 | CGT | AGG |
| 115 | CCG | |
| 120 | | GAT |
| 127 | CGC | AGG |
| 128 | CGC | |
| 131 | ACC | ACC |
| 137 | CTG | CTG |
| 140 | GCT | GCT |
| 143 | CAG | CAG |
| 145 | ACC | ACC |
| 146 | ACC | ACC |
| 147 | CTG | CTG |
| 152 | TTC | TTC |

II. CASSETTE TERMINI

| Cassette # | Bacterial expression |
|---|---|
| I | 73              125<br>arg arg   ...glu  phe   arg<br>TCGT ...GAA TTC CGT<br>AGCA... CTT AAG GCA |

| Cassette # | Mammalian Expression |
|---|---|
| I | 71              125<br>asn leu arg arg   ...glu  phe   arg<br>AAC CTT CGA AGG ...GAA TCC CGTC<br>TTG GAA GCT TCC ...CTT AGG GCAG |

TABLE III-continued

| Cassette # | Bacterial expression |
|---|---|
| II | 126 152 |
| | phe arg phe |
| | AA TTC CGC ... TTC TAG AACTCGAGACTGCA |
| | G GCG ... AAG ATC TTGAGCTCTG |

| Cassette # | Mammalian expression |
|---|---|
| II | 126 152 |
| | phe arg phe |
| | AA TTC CGC ... TTC TAG TAG AACTCGAGA |
| | G GCG ... AAG ATC ATC TTGAGCTCTTTAA |

Alternatively, obtaining the cDNA sequence of a human IL-3-like growth factor can involve cloning the cDNA from a tissue source. The gibbon cDNA sequence of Table I was employed as a probe according to T. Maniatis et al., Molecular Cloning—A Laboratory Manual, Cold Spring Harbor Laboratory (1983) and identified peripheral blood lymphocytes as a human source for isolating mRNA encoding this human IL-3-like polypeptide. Poly A+ RNA is prepared from the peripheral blood lymphocyte source, converted to cDNA and cloned as either a phage or plasmid cDNA library. A human cDNA clone can be identified by hybridization with the gibbon coding sequence of Table I as a DNA probe and a determination of IL-3-like biological properties.

Additional tissue sources which may also be screened for human IL-3-like cDNA include spleen, liver, thymus, tonsils, kidney, and other fresh tissues available from biopsies and cadavers. Of special interest are cases where the tumor may be responsible for elevated hematopoietic cell counts, e.g., leukemia. Additional sources are the cell lines deposited for public use in depositories, e.g. ATCC, or available through government agencies and certain private sources. Exemplary cell lines include transformed T and B cell lines, and cell lines which are not of hematopoietic origin, but generate hematopoietins.

In order to express this human IL-3-like polypeptide, the cDNA encoding it is transferred into an appropriate expression vector, e.g. pCD or pXM, and introduced into selected host cells by conventional genetic engineering techniques as described above. The presently preferred expression system for a biologically active recombinant human IL-3-like polypeptide is stably transformed CHO cells. However, an active polypeptide may be produced intracellularly or extracellularly from bacteria, yeast or insect cells as described in Example IV.

Another alternative method for expressing this human IL-3-like polypeptide is to employ the Bgl II fragment from lambda CSF-16 containing the complete human genomic gene to construct mammalian cell lines expressing the polypeptide, e.g. as described by PCT WO85/20610 for human erythropoietin. In addition, this human genomic gene can be engineered with the appropriate promoter and processing signals for expression in some other heterologous system, e.g. insect promoters for constructing insect cell culture lines. Similarly, this genomic gene may be expressed in yeast or other eukaryotic systems.

EXAMPLE IV
Expression of IL-3-like Growth Factors

A plasmid, pCSF-MLA, is simply constructed by inserting the gibbon sequence of Table I into XhoI-digested pXM as described above. A plasmid with the human sequence, pSHIL-3-1 is constructed synthetically for mammalian expression as described above in Example III. Another plasmid pY3 is made as described above. Each of these plasmids carrying a primate IL-3-like growth factor is then transformed by conventional techniques into a selected host cell for expression of a polypeptide.

A. Mammalian Cell Expression:

To obtain expression of the IL-3-like factors for use in the assays described below, pSHIL-3-1 and pCSF-MLA are transfected onto COS cells. The conditioned medium for the transfected COS cells contained high levels of growth factor activity as described.

Mammalian expression systems and the variants obtained thereby are presently preferred. The mammalian cell expression vectors described herein may. be synthesized by techniques well known to those skilled in this art. The components of the vectors, e.g. bacterial replicons, selection genes, enhancers, promoters, and the like, may be obtained from natural sources or synthesized by known procedures. See, Kaufman et al, *J. Mol. Biol.*, 159:511–521 (1982); and Kaufman, *Proc. Natl. Acad. Sci., U.S.A.*, 82:689–693 (1985). Exemplary host cells are mammalian cells and cell lines, particularly primate cell lines, rodent cell lines and the like, including transformed cell lines. Normal diploid cells, cell strains derived from in vitro culture of primary tissue, as well as primary explants, are also suitable. Candidate cells need not be genotypically deficient in the selection gene so long as the selection gene is dominantly acting. The host cells preferably will be established mammalian cell lines. For stable integration of the vector DNA, and for subsequent amplification of the integrated vector DNA, both by conventional methods, CHO cells are presently preferred. Alternatively, the vector DNA may include all or part of the bovine papilloma virus genome [Lusky et al, *Cell.*, 36:391–401 (1984)] and be carried in cell lines such as C127 mouse cells as a stable episomal element. Other suitable mammalian cell lines include but are not limited to, HeLa, COS-1 monkey cells, mouse L-929 cells, 3T3 lines derived from Swiss, Balb-c or NIH mice, BHK or HaK hamster cell lines and the like.

Stable transformants are then screened for expression of the product by standard immunological or enzymatic assays. The presence of the DNA encoding the variant proteins may be detected by standard procedures such as Southern blotting. Transient expression of the DNA encoding the variants during the several days after introduction of the expression vector DNA into suitable host cells such as COS-1 monkey cells is measured without selection by activity or immunologic assay of the proteins in the culture medium.

One skilled in the art can also construct other mammalian expression vectors comparable to pCSF-MLA and pSHIL-3-1 by, e.g., cutting the DNA sequence of Table I or Table II from the respective plasmids with XhoI and employing well-known recombinant genetic engineering techniques and other known vectors, such as pJL3 and pJL4 [Gough et al., *EMBO J.*, 4:645–653 (1985)] and pMT2 (starting with pMT2-VWF, ATCC #67122; see PCT application PCT/US87/00033). The transformation of these vectors into appropriate host cells can result in expression of the IL-3-like growth factors.

B. Bacterial Expression Systems:

Similarly, one skilled in the art could manipulate the sequences of Tables I and II by eliminating or replacing the mammalian regulatory sequences flanking the coding sequences with bacterial sequences to create bacterial vectors for intracellular or extracellular expression by bacterial cells. The DNA encoding the variant may be further modified as in Example III to contain different codons for bacterial expression as is known in the art. Preferably the sequence is operatively linked in-frame to a nucleotide sequence encoding a secretory leader polypeptide permitting bacterial expression, secretion and processing of the mature variant protein, also as is known in the art. The compounds expressed in mammalian, insect, yeast or bacterial host cells may then be recovered, purified, and/or characterized with respect to physiochemical, biochemical and/or clinical parameters, all by known methods. To construct one such bacterial vector for bacterial expression, a partially synthetic human IL-3 DNA sequence was constructed from the gibbon cDNA and the synthetic bacterial cassettes described in Example III. This sequence was placed into a NdeI/XbaI digested vector paII81 which was deposited Aug. 28, 1984 with the ATCC under accession number 40134. The resulting vector pPLHIL-3-181 was transfected into *E. coli* GL400 and cultured according to the conditions described for GM-CSF in published PCT application 86/00639.

Similarly, the coding sequence of Table I or that of Table II could be cut from pCSF-MLAor pSHIL-3-1, with XhoI and further manipulated (e.g., ligated to other known linkers or modified by deleting non-coding sequences therefrom or altering nucleotides therein by other known techniques). The modified IL-3-like coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and the IL-3-like factor expressed thereby. For a strategy for producing extracellular expression of IL-3-like factors in bacterial cells, see, e.g. European patent application EPA 177, 343.

C. Insect Cell Expression:

Similar manipulations can be performed for the construction of an insect vector [See, e.g., procedures described in published European patent application 155,476] for expression in insect cells. A yeast vector could also be constructed employing yeast regulatory sequences for intracellular or extracellular expression of the proteins of the present invention by yeast cells. [See, e.g., procedures described in published PCT application WO 86 00639 and European patent application EP 123,289.]

EXAMPLE V

Construction of CHO cell lines expressing high levels of Primate IL-3-like Growth Factor One method for producing high levels of the novel primate family of IL-3-like polypeptides of the invention from mammalian cells involves the construction of cells containing multiple copies of the heterologous IL-3-like gene. The heterologous gene can be linked to an amplifiable marker, e.g., the dihydrofolate reductase (DHFR) gene for which cells containing increased gene copies can be selected for propagation in increasing concentrations of methotrexate (MTX) according to the procedures of Kaufman & Sharp, *J. Mol. Biol.*, (1982) supra. This approach can be employed with a number of different cell types.

For example, pY3 contains a human IL-3-like gene in operative association with other plasmid sequences enabling expression thereof. pY3 and the DHFR expression plasmid pAdA26SV(A)3 (Kaufman & Sharp, *Mol. Cell Biol.*, 3(9):1598–1608 (1983) can be co-introduced into DHFR-deficient CHO cells, DUKX-BII, by calcium phosphate coprecipitation and transfection. Alternatively, the gene may be introduced into pMT2 as previously mentioned and the resultant vector used in place of pY3 and pAdA26SV(A)3.

DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., *Mol. Cell Biol.* 5:1750 (1983). Transformants are cloned, and biologically active IL-3-like polypeptide expression is monitored by CML assays. IL-3-like polypeptide expression should increase with increasing levels of MTX resistance. Similar procedures can be followed to produce other members of this family of IL-3-like polypeptides, including the gibbon IL-3-like polypeptides.

EXAMPLE VI

Biological Activities of an IL-3-like Polypeptide

The following assays were performed using both the gibbon polypeptide and the human polypeptide as representative members of the novel family of primate IL-3-like polypeptides of the present invention. However, other members of the family will exhibit IL-3-like biological properties in these same assays or in other assays depending on the number of IL-3-like biological properties displayed by the individual polypeptide.

A. CML Assay

The CML assay was performed essentially according to procedures described in *Blood*, 63(4):904–111 (1984). A stock of cells were obtained from a frozen bag of peripheral blood from a CML patient in stable phase. This bag was thawed and refrozen into 500 aliquots of $15 \times 10^6$ cells/vial. These cells, "CML 8-3", were used to test for the IL-3-like activity of the IL-3-like polypeptides. One vial is thawed quickly at 37 C. the day before the assay is set up. The contents of the vial are then transferred to a 15 ml tube and washed 2 times with 5% Hi Human AB Serum in RPMI (GIBCO,RPMI 1640) [HAB/RPMI]. The cells are incubated overnight in 5% HiHAB/RPMI at 5% $CO_2$ and 37° C. The following day the cells are removed from culture, ficolled, washed, recounted and set aside.

100 ul of 10% HIFCS2/RPMI medium containing the material to be assayed is plated in each well of a microtiter plate. The cells prepared above are spun down and resuspended at a concentration of 1.3 to $2 \times 10^5$ cells/ul in 10% HIFCS/RPMI. 100 uls of cells are plated in each well and incubated in the presence or absence of anti-human GMCSF antibodies at 37 C. in 5% $CO_2$ for 48 or 72 hours. Thereafter 0.5 uCi $^3$H-thymidine is added per well and the wells are incubated for 6 hours at 37 C. Cells are harvested using a filtration manifold device onto GFC Type C filter paper (Schleicher-Schuller), washed with phosphate buffered saline and dried. Filters are then immersed in scintillation fluid and counted for $^3$H uptake.

Based on the thymidine uptake measurement, both the gibbon IL-3-like growth factor and the human IL-3-like growth factor are active in this assay in stimulating the proliferation leukemic blast cells. The gibbon polypeptide was found to be active up to have an average specific activity of $8 \times 10^6$ dilution units per milligram factor. A dilution unit is defined as that dilution of the factor which gives one-half maximal stimulation in the CML assay.

B. Bone Marrow Assays

Human bone marrow assays, employing non-adherent bone marrow cells, were performed as described in G. G. Wong, et al., supra. Conditioned media for both the gibbon and human factors was found to be active in this assay, producing small colonies of apparently granulocytic-type lineage. Also produced upon morphological examination of stained agar cultures were macrophage, granulocyte-macrophage and eosinophil colonies. When this assay is performed in the presence of erythropoietin, the ability of conditioned medium to support the growth of erythroid progenitor cells is demonstrated by the production of red blood cell colonies.

When GM-CSF was compared with the IL-3-like polypeptide in the human bone marrow assay, IL-3-like polypeptide supported the formation of more colonies than GM-CSF, when both polypeptides were in the presence of erythropoietin. The majority of colonies supported by GM-CSF were single lineage; while the polypeptide of the present invention supported the formation of multi-lineage colonies. Similarly, in blast cell colony formation assays, the IL-3-like polypeptide produced greater numbers of blast cell colonies of multiple lineages. GM-CSF in the same assay produced very few secondary colonies.

C. KG-1 Cell Assay

The KG-1 assay was performed as described in G. G. Wong et al, supra. The gibbon IL-3-like polypeptide member of the novel primate family of IL-3-like growth factors produced according to the present invention was active in this assay.

D. Miscellaneous Assays

In an antibody-dependent cell-mediated cytotoxicity assay, the IL-3 -like polypeptide of the present invention stimulated eosinophils to kill antibody-coated tumor target cells in a dose-dependent manner. The polypeptide additionally stimulated eosinophils to phagocytose serumopsonized baker's yeast, and to directly stimulate superoxide anion production by eosinophils. Preliminary results for administering an IL-3-like factor to monkeys show an increase in platelet count and lymphoid cells.

EXAMPLE VII

Purification of IL-3-Like Polypeptide from COS Cell Conditioned Medium

The following procedures are presently employed to obtain homogeneous IL-3-like protein from COS cells, as described in Example IV above.

A. Ion Exchange

COS cell conditioned media [DMEM, 0.5% FBS in roller bottles at a total protein concentration of 200 mg/ml] contained the human IL-3-like polypeptide at a concentration of approximately 2–3 ug/ml. The media is diluted with water until the conductivity is less than 8.0 ms/cm$^2$. An ion exchange cartridge [QAE Zeta Prep] is equilibrated at 4 degrees centigrade with approximately 500 mls 0.1M Tris-Cl, pH8.0 and then two liters of 40 mM Tris-CL, pH7.4. Media was loaded at 40 ml/minute, and the unbound fraction collected. The cartridge was washed with 40 mM Tris-Cl until no further activity washed off. The unbound fraction was concentrated on a diafiltration unit membrane [Amicon YM-10].

B. Lentil Lectin Column

A lentil lectin column was equilibrated in 20 mM Tris, pH7.4, 0.05% Tween-20 at 4 degrees centigrade [Buffer I] and then loaded at 1 column volume per hour. The column was washed with Buffer I to remove non-specifically-bound protein and then bound protein was eluted with Buffer I plus 0.2M alpha-methyl-mannopyranoside. The elution fractions were pooled.

C. Reverse Phase HPLC

This preparation of IL-3-like polypeptide was subjected to reverse phase HPLC at room temperature as described below. The IL-3-like polypeptide preparation was injected onto a RP HPLC column [C4Vydac] equilibrated in 100% Buffer A. Buffer A was 0.1% trifluoroacetic acid [TFA] in water and Buffer B was 0.1% TFA in 95% acetonitrile. The gradient was 0.2%/minute from 45 to 70% Buffer B. The fractions pooled from this gradient were 46.8% B to 47.5% Buffer B. These fractions were speed vacuumed to remove the acetonitrile. In a second reverse phase HPLC step, Buffer A was 0.15% HFBA an water and Buffer B was 0.15% heptafluorobutyric acid [HFBA] in 95% acetonitrile. The gradient was 0.2%/minute from 45 to 70% Buffer B. The fractions pooled from this step were 49% to 51% Buffer B. This fraction eluting from the HPLC was pyrogen free.

EXAMPLE VIII

Analyses of IL-3-Like Polypeptides

A. SDS-PAGE

Following the procedure of R. J. Kaufman and P. A. Sharp., *J. Mol. Biol.* 159:601–621 (1982), $^{35}$S methionine is metabolically incorporated into the polypeptides made by COS cells transfected with pCSF-MLA and COS cells transfected with pY3. SDS polyacrylamide gel electrophoresis (reducing conditions) [U. K. Laemmli, Nature 227:680–685 (1970)] of labeled proteins secreted by the transfected COS-1 cells revealed a distribution of polypeptides with apparent molecular masses ranging between 14 kd and 35 kd for both the gibbon and human factors. This distribution was absent in the mock transfected control sample.

With silver stain after the purification procedures of. Example VI, two major bands of average molecular weights 21,000 and 25,000 appeared in approximately equal amounts for both factors. The differences in the two bands is presently attributed to differences in N-linked glycosylation.

B. Isoelectric Focusing

Native isoelectric focusing of the purified polypeptides of Example VII reveal four species for both the gibbon and human polypeptides, which range in Pi value between pH 6.0 and pH7.6.

C. Superose 6 Fast Protein Liquid Chromatography

The purified fraction from HPLC was run in a gel filtration column [Superose 6] in 20 mM Tris, pH7.4, 200 mM NaCl, and 0.05%Tween-20. This column run revealed one sharp peak of apparent molecular weight of 43 kd for both factors.

Specific Activity in CML Assay

The specific activity of an exemplary gibbon IL-3-like factor in the CML assay described above falls within the range of $2 \times 10^6$ to $1 \times 10^7$ dilution units/mg of polypeptide, with an average of $8 \times 10^6$ dilution unit/mg.

E. N-Terminal Analysis

Analysis of the N-terminal sequence of the gibbon polypeptide was made using automated Edman degradation which demonstrated a level of purity of the factor of 98%.

F. N-Glycanase Treatment

The human and gibbon factors produced in COS cells were treated with the enzyme N-glycanase, which digests the N-linked carbohydrate moieties. Each factor was shown to be purified by this method. The 14–35 kd smear of each factor on the gels was reduced to a single band of 15 kd for the gibbon factor and 20.5 kd for the human factor.

Numerous modifications and variations in practice of this invention are expected to occur to those skilled in the art upon consideration of the foregoing descriptions of preferred embodiments thereof. Such modifications and variations are believed to be encompassed in the appended claims.

What is claimed is:

1. A method of treating leukopenia comprising systemically administering to a leukopenic patient a primate IL-3 polypeptide in an amount sufficient to increase the number of circulating leukocytes in the peripheral blood of said patient.

2. A method for increasing the number of circulating leukocytes in the peripheral blood of a leukopenic patient comprising administering to said patient an amount of a primate IL-3 polypeptide sufficient to increase the number of circulating leukocytes in the peripheral blood.

3. A method for avoiding reduction in the number of circulating leukocytes in the peripheral blood of a patient undergoing chemotherapy comprising administering to said patient an amount of a primate IL-3 polypeptide sufficient to increase the number of circulating leukocytes in the peripheral blood.

4. A method for increasing the number of leukocytes in a suitable cell population comprising administering a primate IL-3 polypeptide to said cell population in vitro.

* * * * *